U S011833327B2

United States Patent
Montero et al.

(10) Patent No.: US 11,833,327 B2
(45) Date of Patent: Dec. 5, 2023

(54) ANALYTE SENSOR CONFIGURATION AND CALIBRATION BASED ON DATA COLLECTED FROM A PREVIOUSLY USED ANALYTE SENSOR

(71) Applicant: MEDTRONIC MINIMED, INC., Northridge, CA (US)

(72) Inventors: Erik Montero, Woodland Hills, CA (US); David C. Antonio, Montrose, CA (US); Eric Allan Larson, Simi Valley, CA (US); Meng Dai Yu, Chatsworth, CA (US); Samuel Finney, Los Angeles, CA (US); Hans K. Wenstad, Santa Clarita, CA (US); David M. Aguirre, Alhambra, CA (US); Andrew P. Lynch, Playa Vista, CA (US); Andrea Varsavsky, Santa Monica, CA (US); Ali Dianaty, Porter Ranch, CA (US)

(73) Assignee: MEDTRONIC MINIMED, INC., Northridge (CA)

( * ) Notice: Subject to any disclaimer, the term of this patent is extended or adjusted under 35 U.S.C. 154(b) by 944 days.

(21) Appl. No.: 16/812,142

(22) Filed: Mar. 6, 2020

(65) Prior Publication Data

US 2021/0275742 A1 Sep. 9, 2021

(51) Int. Cl.
*A61M 5/172* (2006.01)
(52) U.S. Cl.
CPC ... *A61M 5/1723* (2013.01); *A61M 2205/3303* (2013.01); *A61M 2205/702* (2013.01)

(58) Field of Classification Search
CPC ........ A61M 5/1723; A61M 2205/3303; A61M 2205/702; A61M 2005/1726; A61M 2205/33; A61M 2205/3327; A61M 2205/35; A61M 2205/3507; A61M 2205/70; A61B 2560/0223; A61B 5/0024;
(Continued)

(56) References Cited

U.S. PATENT DOCUMENTS

| 4,755,173 A | 7/1988 | Konopka et al. |
| 5,391,250 A | 2/1995 | Cheney, II et al. |

(Continued)

FOREIGN PATENT DOCUMENTS

WO 2019118060 A1 6/2019

*Primary Examiner* — Jason E Flick
(74) *Attorney, Agent, or Firm* — Weaver Austin Villeneuve & Sampson LLP

(57) ABSTRACT

A method of automatically initializing an analyte sensor for a user is disclosed here. A first analyte sensor is operated in a first measurement mode to generate first sensor signals indicative of an analyte level of the user. A second analyte sensor is deployed to measure the analyte level of the user, and is operated in an initialization mode, concurrently with operation of the first analyte sensor in the first measurement mode, to receive sensor configuration data generated by the first analyte sensor. During operation of the second analyte sensor in the initialization mode, the second analyte sensor is calibrated with at least some of the received sensor configuration data. After the calibrating, operation of the second analyte sensor is transitioned from the initialization mode to a second measurement mode during which the second analyte sensor generates second sensor signals indicative of the analyte level of the user.

20 Claims, 5 Drawing Sheets

(58) Field of Classification Search
CPC . A61B 5/1495; A61B 5/14532; A61B 5/6833; A61B 2560/0412; A61B 5/14503; A61B 5/145; A61B 5/14546
See application file for complete search history.

(56) References Cited

U.S. PATENT DOCUMENTS

| | | | |
|---|---|---|---|
| 5,485,408 | A | 1/1996 | Blomquist |
| 5,522,803 | A | 6/1996 | Teissen-Simony |
| 5,665,065 | A | 9/1997 | Colman et al. |
| 5,800,420 | A | 9/1998 | Gross et al. |
| 5,807,375 | A | 9/1998 | Gross et al. |
| 5,925,021 | A | 7/1999 | Castellano et al. |
| 5,954,643 | A | 9/1999 | Van Antwerp et al. |
| 6,017,328 | A | 1/2000 | Fischell et al. |
| 6,186,982 | B1 | 2/2001 | Gross et al. |
| 6,246,992 | B1 | 6/2001 | Brown |
| 6,248,067 | B1 | 6/2001 | Causey, III et al. |
| 6,248,093 | B1 | 6/2001 | Moberg |
| 6,355,021 | B1 | 3/2002 | Nielsen et al. |
| 6,379,301 | B1 | 4/2002 | Worthington et al. |
| 6,544,212 | B2 | 4/2003 | Galley et al. |
| 6,558,351 | B1 | 5/2003 | Steil et al. |
| 6,591,876 | B2 | 7/2003 | Safabash |
| 6,641,533 | B2 | 11/2003 | Causey, III et al. |
| 6,736,797 | B1 | 5/2004 | Larsen et al. |
| 6,749,587 | B2 | 6/2004 | Flaherty |
| 6,766,183 | B2 | 7/2004 | Walsh et al. |
| 6,801,420 | B2 | 10/2004 | Talbot et al. |
| 6,804,544 | B2 | 10/2004 | Van Antwerp et al. |
| 6,892,085 | B2 | 5/2005 | McIvor et al. |
| 7,003,336 | B2 | 2/2006 | Holker et al. |
| 7,029,444 | B2 | 4/2006 | Shin et al. |
| 7,066,909 | B1 | 6/2006 | Peter et al. |
| 7,137,964 | B2 | 11/2006 | Flaherty |
| 7,303,549 | B2 | 12/2007 | Flaherty et al. |
| 7,399,277 | B2 | 7/2008 | Saidara et al. |
| 7,442,186 | B2 | 10/2008 | Blomquist |
| 7,468,033 | B2 | 12/2008 | Van Antwerp et al. |
| 7,602,310 | B2 | 10/2009 | Mann et al. |
| 7,647,237 | B2 | 1/2010 | Malave et al. |
| 7,699,807 | B2 | 4/2010 | Faust et al. |
| 7,727,148 | B2 | 6/2010 | Talbot et al. |
| 7,785,313 | B2 | 8/2010 | Mastrototaro |
| 7,806,886 | B2 | 10/2010 | Kanderian, Jr. et al. |
| 7,819,843 | B2 | 10/2010 | Mann et al. |
| 7,828,764 | B2 | 11/2010 | Moberg et al. |
| 7,879,010 | B2 | 2/2011 | Hunn et al. |
| 7,890,295 | B2 | 2/2011 | Shin et al. |
| 7,892,206 | B2 | 2/2011 | Moberg et al. |
| 7,892,748 | B2 | 2/2011 | Norrild et al. |
| 7,901,394 | B2 | 3/2011 | Ireland et al. |
| 7,942,844 | B2 | 5/2011 | Moberg et al. |
| 7,946,985 | B2 | 5/2011 | Mastrototaro et al. |
| 7,955,305 | B2 | 6/2011 | Moberg et al. |
| 7,963,954 | B2 | 6/2011 | Kavazov |
| 7,977,112 | B2 | 7/2011 | Burke et al. |
| 7,979,259 | B2 | 7/2011 | Brown |
| 7,985,330 | B2 | 7/2011 | Wang et al. |
| 8,024,201 | B2 | 9/2011 | Brown |
| 8,100,852 | B2 | 1/2012 | Moberg et al. |
| 8,114,268 | B2 | 2/2012 | Wang et al. |
| 8,114,269 | B2 | 2/2012 | Cooper et al. |
| 8,137,314 | B2 | 3/2012 | Mounce et al. |
| 3,181,849 | A1 | 5/2012 | Bazargan et al. |
| 8,182,462 | B2 | 5/2012 | Istoc et al. |
| 8,192,395 | B2 | 6/2012 | Estes et al. |
| 8,195,265 | B2 | 6/2012 | Goode, Jr. et al. |
| 8,202,250 | B2 | 6/2012 | Stutz, Jr. |
| 8,207,859 | B2 | 6/2012 | Enegren et al. |
| 8,226,615 | B2 | 7/2012 | Bikovsky |
| 8,257,259 | B2 | 9/2012 | Brauker et al. |
| 8,267,921 | B2 | 9/2012 | Yodfat et al. |
| 8,275,437 | B2 | 9/2012 | Brauker et al. |
| 8,277,415 | B2 | 10/2012 | Mounce et al. |
| 8,292,849 | B2 | 10/2012 | Bobroff et al. |
| 8,298,172 | B2 | 10/2012 | Nielsen et al. |
| 8,303,572 | B2 | 11/2012 | Adair et al. |
| 8,305,580 | B2 | 11/2012 | Aasmul |
| 8,308,679 | B2 | 11/2012 | Hanson et al. |
| 8,313,433 | B2 | 11/2012 | Cohen et al. |
| 8,318,443 | B2 | 11/2012 | Norrild et al. |
| 8,323,250 | B2 | 12/2012 | Chong et al. |
| 8,343,092 | B2 | 1/2013 | Rush et al. |
| 8,352,011 | B2 | 1/2013 | Van Antwerp et al. |
| 8,353,829 | B2 | 1/2013 | Say et al. |
| 9,295,786 | B2 | 3/2016 | Gottlieb et al. |
| 2007/0123819 | A1 | 5/2007 | Mernoe et al. |
| 2008/0312859 | A1 | 12/2008 | Skyggebjerg et al. |
| 2009/0299301 | A1 | 12/2009 | Gottlieb et al. |
| 2010/0160861 | A1 | 6/2010 | Causey, III et al. |
| 2012/0277566 | A1* | 11/2012 | Kamath ............... A61B 5/1451 600/365 |
| 2013/0317332 | A1 | 11/2013 | Feldman |
| 2017/0290535 | A1 | 10/2017 | Rao et al. |

\* cited by examiner

ANALYTE SENSOR CONFIGURATION AND CALIBRATION BASED ON DATA COLLECTED FROM A PREVIOUSLY USED ANALYTE SENSOR

TECHNICAL FIELD

Embodiments of the subject matter described herein relate generally to an analyte sensor for monitoring a physiological characteristic of a user, such as blood glucose level. More particularly, the disclosed subject matter relates to an analyte sensor device and related operating methodologies for initializing and calibrating the analyte sensor device when newly deployed.

BACKGROUND

The prior art includes a wide variety of medical devices and components, and associated operating methodologies. For example, physiological analyte sensors are generally known in the art for use in a variety of specialized applications. In this regard, thin film electrochemical sensors are used to test analyte levels in patients. More specifically, thin film sensors have been designed for use in obtaining an indication of blood glucose (BG) levels and monitoring BG levels in a diabetic patient, with the distal segment portion of the sensor positioned subcutaneously in direct contact with patient extracellular fluid. Such readings can be especially useful in adjusting a treatment regimen which typically includes regular administration of insulin to the patient.

Conventional glucose sensor sets typically include three main components: a disposable sensor with its mounting base; a durable, rechargeable transmitting device that is coupled to cooperate with the sensor; and a sensor insertion tool. The sensor component must be replaced on a regular basis, usually about once a week, once every ten days, or the like. When the sensor component is replaced, the user suspends any continuous glucose monitoring to recharge the transmitting device and to prepare the new sensor component for use. The sensor insertion process is often long and complex. In some scenarios, the user may have to wait over an hour before the new sensor is ready to provide glucose readings, which results in a break of the monitoring process. Moreover, newly deployed glucose sensors must be calibrated against a reliable blood glucose measurement baseline, e.g., a fingerstick blood sample or an accurate and trusted glucose sensor reading.

Accordingly, it is desirable to provide an improved analyte sensor device and more convenient and efficient sensor deployment methodologies that make it easier and less time consuming to deploy and use a new sensor that replaces an old sensor. Furthermore, other desirable features and characteristics will become apparent from the subsequent detailed description and the appended claims, taken in conjunction with the accompanying drawings and the foregoing technical field and background.

BRIEF SUMMARY

Disclosed here is a method of automatically initializing an analyte sensor for a user. An exemplary embodiment of the method involves the steps of: operating a first analyte sensor in a first measurement mode to generate first sensor signals indicative of an analyte level of the user; deploying a second analyte sensor to measure the analyte level of the user; operating the second analyte sensor in an initialization mode, concurrently with operation of the first analyte sensor in the first measurement mode, to receive sensor configuration data generated by the first analyte sensor; during operation of the second analyte sensor in the initialization mode, calibrating the second analyte sensor with at least some of the received sensor configuration data; and after the calibrating, transitioning operation of the second analyte sensor from the initialization mode to a second measurement mode during which the second analyte sensor generates second sensor signals indicative of the analyte level of the user.

Also disclosed here is an analyte sensor device. An exemplary embodiment of the sensor device includes: a housing; an electronics assembly inside the housing; and a sensor element extending from the housing and electrically coupled to the electronics assembly, wherein the sensor element provides sensor signals indicative of an analyte level of a user when the analyte sensor device is deployed at the user. The electronics assembly includes at least one processor device and non-transitory processor-readable media operatively associated with the at least one processor device. The processor-readable media stores executable instructions configurable to cause the at least one processor device to perform a method that involves the steps of: activating an initialization mode of the analyte sensor device; during operation of the analyte sensor device in the initialization mode, receiving sensor configuration data for processing by the electronics assembly, the sensor configuration data originating at a second analyte sensor device deployed at, or previously deployed at, the user; during operation of the analyte sensor device in the initialization mode, configuring at least one sensor parameter of the analyte sensor device, based on the received sensor configuration data; and after the configuring, transitioning operation of the analyte sensor device from the initialization mode to a measurement mode during which the analyte sensor device generates sensor signals indicative of the analyte level of the user.

Also disclosed here is another method of automatically initializing an analyte sensor for a user. An exemplary embodiment of the method involves the steps of: activating a new analyte sensor to measure an analyte level of the user; during operation of the new analyte sensor in an initialization mode, receiving sensor configuration data at the new analyte sensor, the sensor configuration data originating at an old analyte sensor deployed at, or previously deployed at, the user; during operation of the new analyte sensor in the initialization mode, configuring at least one sensor parameter of the new analyte sensor, based on the received sensor configuration data; and after the configuring, transitioning operation of the new analyte sensor from the initialization mode to a first measurement mode during which the new analyte sensor generates first sensor signals indicative of the analyte level of the user.

This summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
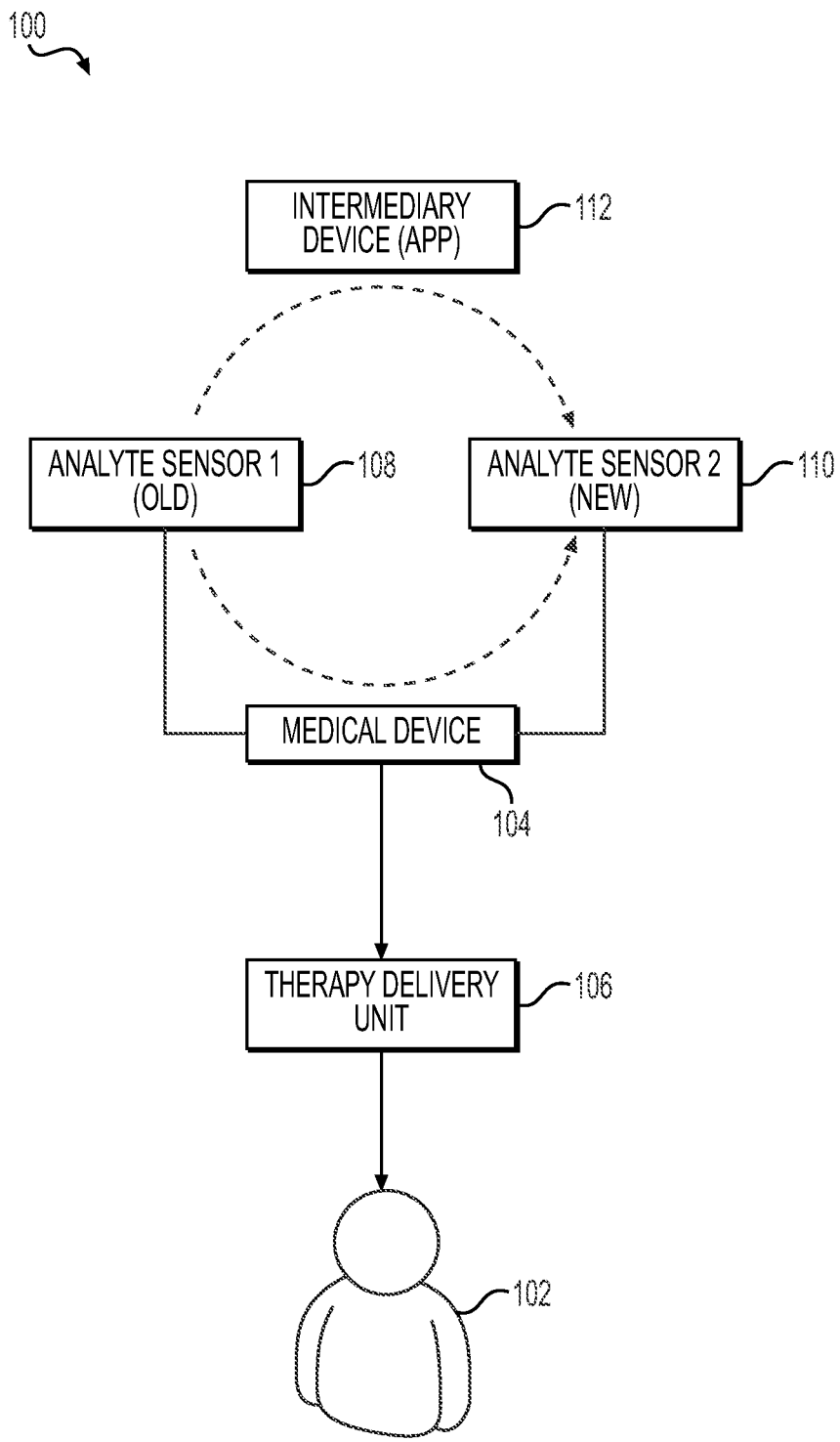
FIG. 1 is a simplified block diagram representation of a medical device system that is configured, arranged, and operated in accordance with an exemplary embodiment of the invention.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software or firmware, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

The subject matter described here relates to a physiological analyte sensor device and related operating methodologies. The non-limiting exemplary embodiment described below relates to a continuous glucose sensor of the type used by diabetic patients. It should be appreciated that the concepts, operating methodologies, and calibration techniques mentioned here need not be limited to use with glucose sensors and, indeed, the concepts and technology described with reference to a glucose sensor could also be used with other medical devices, other physiological characteristic sensor types, other medical components or supplies, and the like.

For the sake of brevity, conventional aspects and technology related to glucose sensors and glucose sensor fabrication may not be described in detail here. A glucose sensor of the type described here may be realized as an electrochemical sensor that employs the glucose oxidase enzyme. Sensors that use glucose oxidase to effect a reaction of glucose and oxygen are known, and such glucose sensors will not be described in detail here. In this regard, known and/or conventional aspects of glucose sensors and their manufacturing may be of the type described in, but not limited to: U.S. Pat. Nos. 5,391,250, 6,892,085, 7,468,033, and 7,602,310, and United States patent application numbers 2009/0299301 and 2017/0290535 (which are incorporated by reference herein).

FIG. 1 is a simplified block diagram representation of a medical device system 100 that is configured, arranged, and operated in accordance with an exemplary embodiment of the invention. The system 100 supports a user 102 of a medical device 104 that regulates the delivery or administration of medication to the user 102. Although not always required, the medical device 104 may include or cooperate with a therapy delivery unit 106 that is attached to, worn by, or implanted in the body of the user 102 to facilitate the delivery of the medication to the user 102. The medical device 104 includes or cooperates with an analyte sensor device, which measures an analyte level of the user 102. In practice, the analyte sensor device is a disposable component that must be replaced on a regular basis. Accordingly, FIG. 1 depicts an old analyte sensor device 108 (a first analyte sensor) and a new analyte sensor device 110 (a second analyte sensor), wherein the new analyte sensor device 110 replaces the old analyte sensor device 108 at an appropriate time. The embodiment of the system 100 shown in FIG. 1 also includes or cooperates with an intermediary device 112 having one or more software applications that support the techniques and methodologies described in more detail herein. The intermediary device 112 can be realized as a mobile computing device, a smartphone, a patient monitor device, a wearable computing device such as a smart watch, a video game device, a media player device, a medical device, or the like. In some implementations, the system 100 need not include the intermediary device 112 if the medical device 104 includes the features and functions of the intermediary device 112. In other words, the medical device 104 may also serve as the intermediary device.

In accordance with the non-limiting example described here, the medical device 104 is realized as a medication infusion device configured to regulate delivery of a medication fluid to the user 102, wherein the therapy delivery unit 106 is realized as a fluid infusion unit having a fluid delivery cannula or needle that is deployed in the skin or body of the user 102. The medical device 104 regulates delivery of the medication to the user based on sensor signals provided by the analyte sensor device(s). In certain embodiments, the medical device 104 is an insulin infusion device, the therapy delivery unit 106 is a disposable/replaceable insulin infusion set that is fluidly coupled to the insulin infusion device, and the analyte sensor devices 108, 110 are continuous glucose sensor devices. In this context, the insulin infusion device, the glucose sensor devices, and the infusion set are components of an insulin infusion system that is used by the patient to treat diabetes.

At least some of the components of the system 100 are communicatively coupled with one another to support data communication as needed. For this particular example, the medical device 104 can wirelessly communicate with the analyte sensor devices 108, 110 via suitable data communication links and communication protocols. Moreover, the intermediary device 112 can wirelessly communicate with the analyte sensor devices 108, 110 via suitable data communication links and communication protocols. In certain embodiments, the analyte sensor devices 108, 110 can wirelessly communicate directly with each other via a suitable data communication link and communication protocol. Other configurations and topologies are also contemplated here, such as a system that includes additional intermediary, interface, or data repeating devices in the data path between a sending device and a receiving device.

Depending on the particular embodiment and application, the system 100 can include or cooperate with other devices, systems, and sources of input data. For example, in certain embodiments the system 100 includes one or more sources of contextual information or data, which may include, without limitation: activity tracker devices or apps; meal logging devices or apps; mood tracking devices or apps; and the like.

FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a near-field data communication link; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the network.

Figure 2:
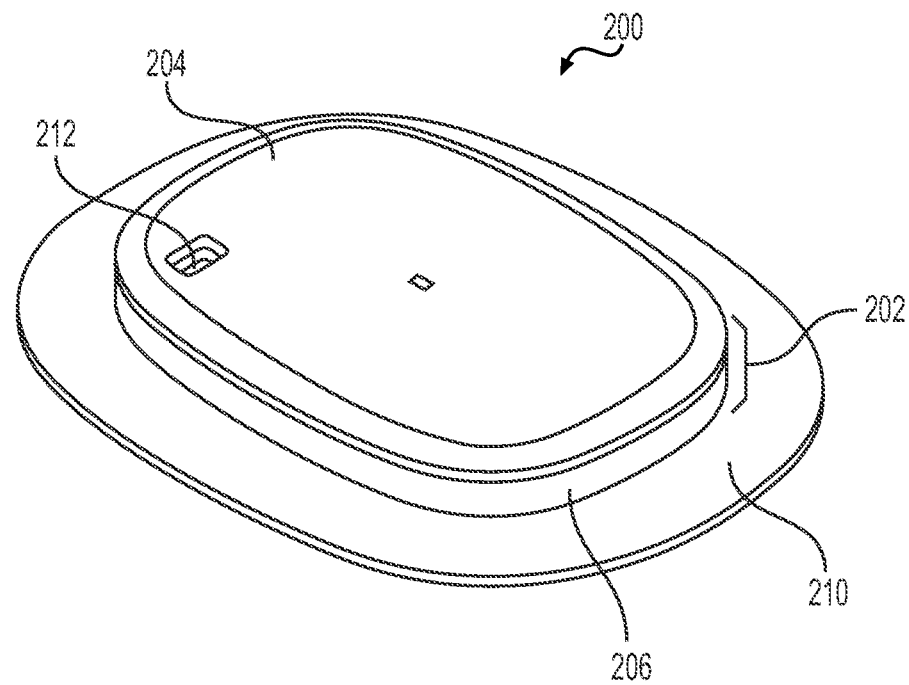
FIG. 2 is a perspective top view of an exemplary embodiment of an analyte sensor device.
Figure 3:
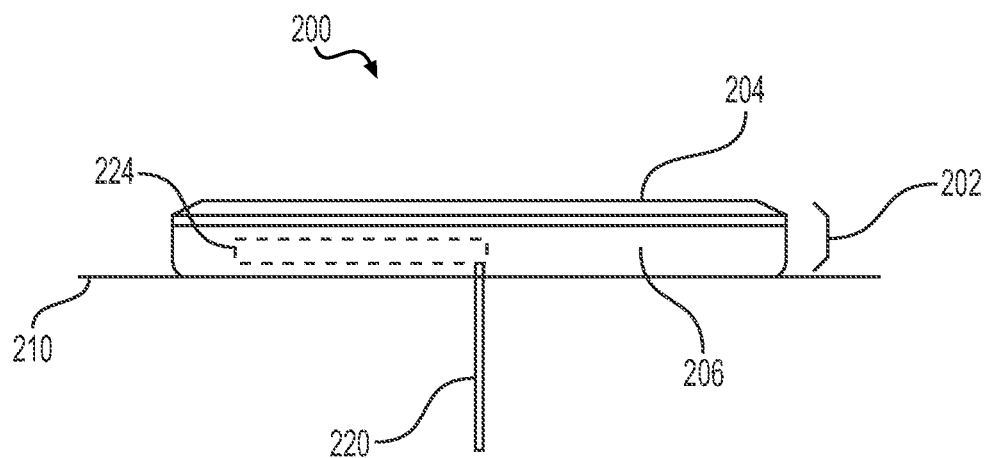
FIG. 3 is a side view of the analyte sensor device shown in FIG. 2.

FIG. 2 is a perspective top view of an exemplary embodiment of an analyte sensor device 200 (which is suitable for use in the medical device system 100), and FIG. 3 is a side view of the analyte sensor device 200. The illustrated embodiment of the analyte sensor device 200 includes a housing 202 having an upper housing 204 with an upper major wall inside the upper housing 204, and a lower housing 206 with a lower major wall inside the lower housing 206, where the upper and lower major walls oppose each other. The housing 202 is shown as generally rectangular, but other shapes, such as square shapes, circular shapes, and polygon shapes, can be used according to the size of the components housed inside and to increase comfort levels on the skin. The housing 202 has a low profile to decrease visibility through clothing and also to decrease discomfort and interference from the sensing device when it is worn on a patient's skin.

The housing 202 may be attached to an adhesive patch 210 for press-on adhesive mounting onto the skin of the user. The patch 210 may be sized such that it has as much adhesion to skin as possible while not being too large for comfort or to easily fit on a patient. It should be appreciated that alternative methods or techniques for attaching the housing 202 to the skin of a patient, other than an adhesive patch 210, also may be contemplated. The housing 202 may be made out of a suitable rigid plastic that can safely and securely hold electrical components of the analyte sensor device 200. In this configuration, the upper housing 204 includes a small opening 212 for pass through of a battery pull tab (not shown) used to block an internal battery from contacting the electronic battery contacts prior to use, thus preventing battery depletion and preventing premature activation of the analyte sensor device. In certain embodiments, removal of the pull tab causes the sensor device 200 to activate or enter an initialization mode (as described in more detail below).

The adhesive patch 210 may be bonded to the lower housing 206 along the entire footprint of the lower housing 206, or over just a portion, such as the perimeter of the lower housing 206. The patch 210 may be ultrasonically welded to the lower housing 206 or adhered, for example, by a double-sided adhesive. In certain configurations, the adhesive patch 210 extends further than the edge of the lower housing 206.

FIG. 3 shows a side view of the analyte sensor device 200 with a thin film sensor element 220 extending from the housing 202 and through the patch 210, which may include a hole for the sensor element 220 to pass through. As shown in FIG. 3, the sensor element 220 includes a relatively thin and elongated element which can be constructed according to so-called thin mask techniques to include elongated conductive elements embedded or encased between layers of a selected insulative sheet material such as a polyimide film or sheet. The proximal end or head of the sensor element 220 is relatively enlarged and defines electrical contacts for electrical coupling to an electronics assembly 224 (depicted in phantom lines in FIG. 3) that resides inside the housing 202. An opposite or distal segment of the sensor element 220 includes a plurality of exposed sensor electrodes that contact body fluid and/or tissue when the sensor distal segment is placed into the body of the user. The sensor electrodes convey sensor signals representative of the measured analyte level of interest. Thus, the sensor element 220 provides sensor signals that are indicative of the analyte level of the user when the analyte sensor device 200 is deployed at the user.

The sensor signals are transmitted in an ongoing manner from the analyte sensor device 200 (which includes a wireless transmitter) to an appropriate destination device for recordation, processing, and/or display as a monitored patient condition. Referring again to FIG. 1, the analyte sensor device 200 may be suitably configured to transmit sensor signals to the medical device 104, to the intermediary device 112, and/or to another sensor device. Further description of flexible thin film sensors of this general type may be found in U.S. Pat. No. 5,391,250, which is herein incorporated by reference. Sensor electronics including wireless transmitters are discussed, for example, in U.S. Pat. No. 7,602,310, which is herein incorporated by reference.

Figure 4:
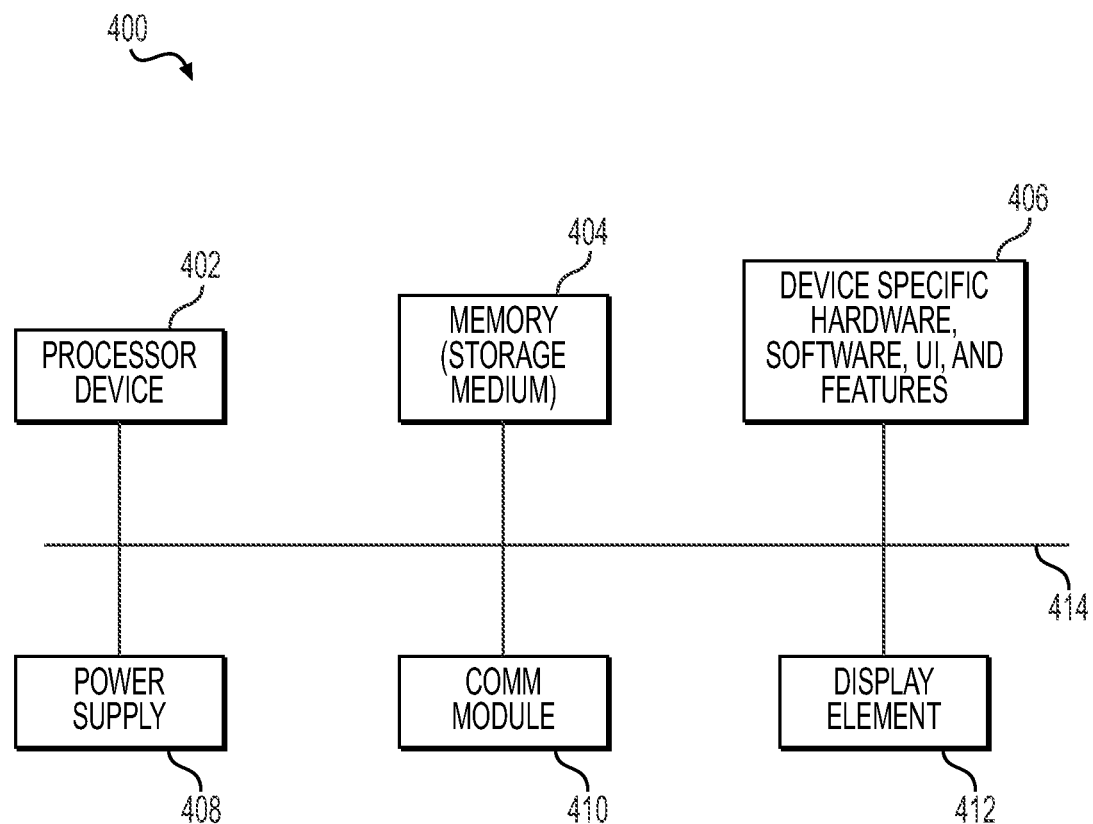
FIG. 4 is a simplified block diagram representation of an exemplary embodiment of a computer-based or processor-based device suitable for deployment in the system shown in FIG. 1.

In accordance with certain embodiments, the medical device 104, the intermediary device 112, and each analyte sensor device 108, 110 can be implemented as a computer-based or a processor-based device, system, or component having suitably configured hardware and software written to perform the functions and methods needed to support the features described herein. In this regard, FIG. 4 is a simplified block diagram representation of an exemplary embodiment of a computer-based or processor-based device 400 that is suitable for deployment in the system shown in FIG. 1.

The illustrated embodiment of the device 400 is intended to be a high-level and generic representation of one suitable platform. In this regard, any computer-based or processor-based component of the system 100 can utilize the architecture of the device 400. The illustrated embodiment of the device 400 generally includes, without limitation: at least one processor device 402; a suitable amount of memory 404; device-specific hardware, software, firmware, user interface (UI), and/or features 406; a power supply 408 such as a disposable or rechargeable battery; a communication module 410; and a display element 412. Of course, an implementation of the device 400 may include additional elements, components, modules, and functionality configured to support various features that are unrelated to the subject matter described here. For example, the device 400 may include certain features and elements to support conventional functions that might be related to the particular implementation and deployment of the device 400. In practice, the elements of the device 400 may be coupled together via a bus or any suitable interconnection architecture 414.

The processor device 402 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. Moreover, the processor device 402 may be implemented as a combination of computing devices, e.g., a combination of a digital signal processor and a microprocessor, a plurality of microprocessors, one or more microprocessors in conjunction with a digital signal processor core, or any other such configuration.

The memory 404 may be realized as RAM memory, flash memory, EPROM memory, EEPROM memory, registers, a hard disk, a removable disk, a CD-ROM, or any other form of storage medium known in the art. In this regard, the memory 404 can be coupled to the processor device 402 such that the processor device 402 can read information from, and write information to, the memory 404. In the alternative, the memory 404 may be integral to the processor device 402. As an example, the processor device 402 and the memory 404 may reside in an ASIC. At least a portion of the memory 404 can be realized as a computer storage medium that is operatively associated with the processor device 402, e.g., a tangible computer-readable medium having computer-executable instructions stored thereon. The computer-executable instructions, when read and executed by the processor device 402, cause the device 400 to perform certain tasks, operations, functions, and processes that are specific to the particular embodiment. In this regard, the memory 404 may represent one suitable implementation of such computer-readable media. Alternatively or additionally, the device 400 could receive and cooperate with computer-readable media (not separately shown) that is realized as a portable or mobile component or platform, e.g., a portable hard drive, a USB flash drive, an optical disc, or the like.

The device-specific hardware, software, firmware, UI, and features 406 may vary from one embodiment of the device 400 to another. For example, the device-specific hardware, software, firmware, UI, and features 406 will support: medical device operations when the device 400 is realized as a medical device (e.g., an insulin infusion pump); smartphone features and functionality when the device 400 is realized as a smartphone; sensor operations and features when the device 400 is realized as an analyte sensor; etc. In practice, certain portions or aspects of the device-specific hardware, software, firmware, UI, and features 406 may be implemented in one or more of the other blocks depicted in FIG. 4.

If present, the UI of the device 400 may include or cooperate with various features to allow a user to interact with the device 400. Accordingly, the UI may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 400. The UI may include one or more graphical user interface (GUI) control elements that enable a user to manipulate or otherwise interact with an application via the display element 412.

The communication module 410 facilitates data communication between the device 400 and other components as needed during the operation of the device 400. In the context of this description, the communication module 410 can be employed to transmit or stream device-related control data, patient-related data, device-related status or operational data, therapy recommendations, infusion device adjustment recommendations and related control instructions, and the like. It should be appreciated that the particular configuration and functionality of the communication module 410 can vary depending on the hardware platform and specific implementation of the device 400. Accordingly, with reference to FIG. 1, the communication module of the intermediary device 112 can be utilized to receive and transmit sensor data. Moreover, the communication module of the medical device 104 can be used to receive sensor data from an active analyte sensor device 108, 110. In practice, an embodiment of the device 400 may support wireless data communication and/or wired data communication, using various data communication protocols. For example, the communication module 410 could support one or more wireless data communication protocols, techniques, or methodologies, including, without limitation: RF; IrDA (infrared); Bluetooth; Bluetooth Low Energy (BLE); ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication module 410 could support one or more wired/cabled data communication protocols, including, without limitation: Ethernet; powerline; home network communication protocols; USB; IEEE 1394 (Firewire); hospital network communication protocols; and proprietary data communication protocols.

The display element 412 is suitably configured to enable the device 400 to render and display various screens, recommendation messages, notifications, GUIs, GUI control elements, drop down menus, auto-fill fields, text entry fields, message fields, or the like. Of course, the display element 412 may also be utilized for the display of other information during the operation of the device 400, as is well understood.

Notably, the specific configuration, operating characteristics, size, resolution, and functionality of the display element 412 can vary depending upon the practical implementation of the device 400.

The disclosed subject matter relates to a system and related operating methodology for initializing, configuring, and/or calibrating an analyte sensor device (such as a continuous glucose sensor) based on sensor data from a previously deployed sensor device of the same type. Continuous glucose monitoring sensors require blood glucose measurements (samples) for calibration. However, fingerstick blood glucose measurements can be unpleasant and burdensome to patients. Disposable glucose sensor devices allow patients to receive uninterrupted sensor glucose data by way of "sensor overlap" during which the patient deploys a new sensor and allows it to initialize and warm up while an existing sensor is still actively providing valid sensor glucose data. The methodology presented here leverages sensor data from the old sensor device for purposes of calibrating and configuring the new sensor device. During the sensor overlap period, the currently deployed (old) sensor provides sensor data that is received by the new sensor. The disclosed system may use an intermediary communication device to facilitate the transfer of sensor data, or it may use direct communication between the two sensor devices. The new sensor device uses the received sensor data to perform initial calibration and/or configuration of sensor operating parameters without requiring a new blood glucose sample.

The disclosed methodology improves the experience of the patient by reducing the number of fingerstick measurements and by reducing the amount of patient interaction required to activate a newly deployed sensor. Moreover, the disclosed methodology reduces the time a user is without therapy. As explained in more detail below, the user will receive uninterrupted sensor readings and can therefore remain in an automatic (closed loop therapy) operating mode while a new sensor is deployed.

The disclosed system and methodologies can also be used to transfer sensor data for use with features and operations other than sensor calibration. For example, the received sensor data can be used to reduce the duration of sensor initialization or warmup, improve sensor accuracy and characterization of the user, and detect out-of-box inconsistencies or inaccuracies of newly deployed sensors. In certain implementations, the disclosed subject matter is applicable to continuous glucose sensor enabled insulin infusion pump systems and standalone continuous glucose monitoring systems. Moreover, the disclosed subject matter can also be utilized with any suitably configured medical device system that includes or cooperates with disposable sensor devices.

Figure 5:
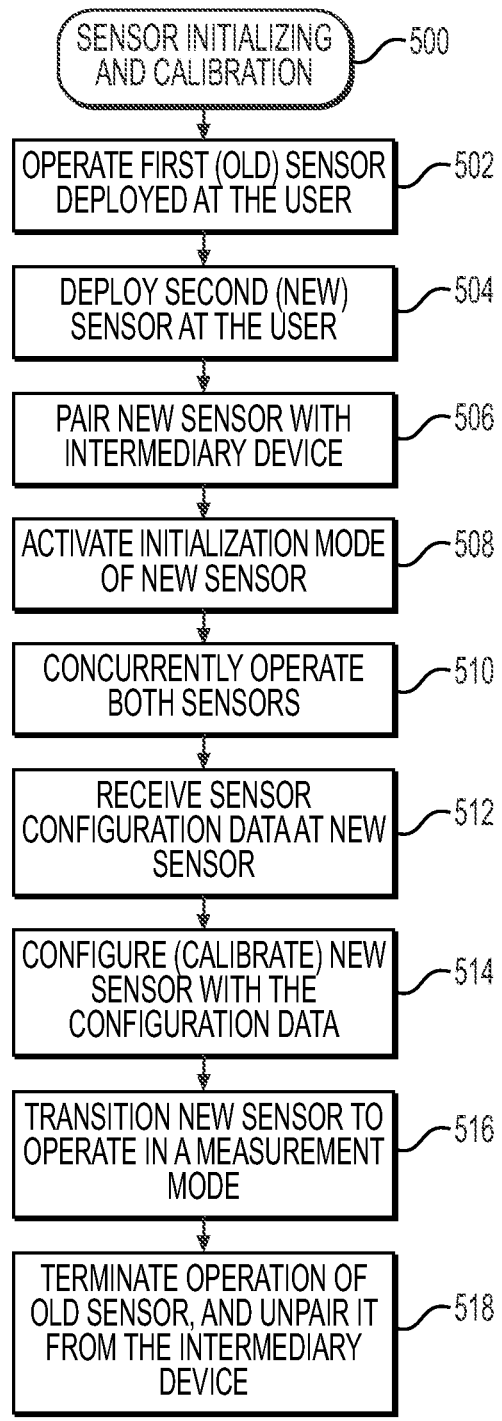
FIG. 5 is a flow chart that illustrates an exemplary embodiment of a sensor initializing and calibration process.

FIG. 5 is a flow chart that illustrates an exemplary embodiment of a sensor initializing and calibration process 500. The various tasks performed in connection with process 500 may be performed by software, hardware, firmware, or any combination thereof. For illustrative purposes, the following description of process 500 may refer to elements mentioned above in connection with FIGS. 1-4. In practice, portions of process 500 may be performed by different elements of the described system, e.g., a sensor device, a medical device, an intermediary device, a smartphone app, or the like. It should be appreciated that process 500 may include any number of additional or alternative tasks, the tasks shown in FIG. 5 need not be performed in the illustrated order, and process 500 may be incorporated into a more comprehensive procedure or process having additional functionality not described in detail herein. Moreover, one or more of the tasks shown in FIG. 5 could be omitted from an embodiment of the process 500 as long as the intended overall functionality remains intact.

The process 500 assumes that a first (old) analyte sensor device is operating while deployed at the user (task 502). More specifically, the old analyte sensor device is operating in a measurement mode to generate corresponding sensor signals that are indicative of an analyte level of the user. While operating in the measurement mode, the sensor signals generated by the old analyte sensor device can be saved at the old analyte sensor device, transmitted to a medical device, transmitted to an intermediary device, uploaded to a cloud-based computing device, or the like.

The process 500 continues by deploying a second (new) analyte sensor device to measure the analyte level of the user (task 504). For this example, the new analyte sensor device is deployed onto the body of the user by way of an insertion component using conventional insertion techniques. The new analyte sensor is deployed and prepared for usage while the old analyte sensor device remains operating in the measurement mode. In connection with deployment of the new analyte sensor, the process 500 pairs the new analyte sensor device with the intermediary device and/or with the medical device (task 506), and activates an initialization mode of the new analyte sensor (task 508). Pairing of the new analyte sensor device establishes a secure data communication link to facilitate transmission of sensor configuration data from the intermediary device to the new analyte sensor device, and to facilitate transmission of sensor data from the new analyte sensor device to the intermediary device if so desired.

The process 500 concurrently operates both analyte sensor devices during an "overlap" period (task 510). The concurrent overlap period corresponds to operation of the old analyte sensor device in its measurement mode, along with operation of the new analyte sensor in its initialization mode or following the initialization mode. After the new analyte sensor device enters the initialization mode, it can communicate its "warm-up" status to a destination device, such as the intermediary device. The intermediary device can respond to the communicated status by requesting information from the old analyte sensor device. Thus, during this concurrent overlap period, the new analyte sensor device receives sensor configuration data that was generated by the old analyte sensor device (task 512). For the exemplary embodiment presented here, the new analyte sensor device receives the sensor configuration data indirectly, via the intermediary device (which may serve as a data pass-through component in this context). In other embodiments, however, the new analyte sensor device receives the sensor configuration data directly from the old analyte sensor device, in accordance with a secure point-to-point data communication protocol. Thus, the sensor configuration data originating at the old analyte sensor device is transferred to the new analyte sensor device for processing, handling, and storage as needed.

The configuration/calibration data provided by the old analyte sensor device may include any of the following information, without limitation:

One or more prior measurement samples and their age in relation to a calibration transfer time (absolute time (UTC), device (CGM or pump) reference time, or the like). Calibration transfer time is defined as the time at which the calibration data is retrieved from the old sensor device. In some embodiments, the data must be retrieved from the old sensor device and written to the new sensor device within a fixed or predetermined window of valid time. The timing data is not adjusted to compensate for the time elapsed between these events. In other embodiments, a display device may adjust the timing information of each sample to compensate for an extended period of elapsed time between the two data exchange events (retrieval from the old sensor device and transmission to the new sensor device).

One or more prior measurement samples and their age in relation to a sensor reference time (sensor start time or other epoch known only to the old sensor device). The data retrieved may also include the calibration transfer time in relation to the sensor reference time. In some embodiments, the data must be retrieved from the old sensor device and written to the new sensor device within a fixed or predetermined window of valid time. The timing data is not adjusted to compensate for the time elapsed between these events. In other embodiments, a display device may adjust the calibration transfer time information or the timing information of each sample to compensate for an extended period of elapsed time between the two data exchange events (retrieval from the old sensor device and transmission to the new sensor device).

One or more prior measurement samples with absolute timestamps. These timestamps may be in a time scale maintained by the display device, or a global time reference (UTC, Unix epoch time, etc.).

One or more prior measurement samples with no timing information.

One or more prior measurement samples with predetermined time separation (e.g., an array of measurements at 30-minute intervals).

Additional context, status, or device health data.

The measurement samples may include any of the following, without limitation: glucose concentrations derived from blood; glucose concentrations derived from interstitial fluid; glucose concentration rate-of-change data; sensor current values; sensor electrode voltages; EIS results; other state data from the sensor device.

Referring again to FIG. 5, during operation of the new analyte sensor device in its initialization mode, and concurrently with operation of the old analyte sensor device in its measurement mode, the process 500 continues by configuring at least one sensor parameter of the new analyte sensor device (task 514). Configuring the new analyte sensor device is based on at least some of the received sensor configuration data. In this context, the received sensor configuration data is used to adjust settings, modify control algorithms or adjust algorithm constants or factors, adjust preferences, and/or adjust certain variables that affect the performance, output, or operation of the new analyte sensor device. For the exemplary embodiment described here, the configuring performed at task 514 includes calibration of the new analyte sensor device using at least some of the received sensor configuration data.

In certain embodiments, the new analyte sensor device reviews the received sensor configuration data to determine whether or not the data can be used for calibration. If the received data is suitable for calibration, then sensor calibration proceeds with the received data. If the new analyte sensor device determines that the received data is deficient, is otherwise unsuitable for use with calibration, or should be supplemented, then it can generate an indication or message to prompt calibration in accordance with conventional methodologies (e.g., obtain an analyte sample from the user). Checking the received sensor configuration data may involve the application of validity tests to the data or its associated metadata, such as timestamps. In practice, the determination can be related to the specific sensor algorithm.

For example, the algorithm may do a calibration error check to review an old sensor glucose sample divided by the sensor current signal (commonly referred to as ISIG) to determine whether the ratio is within certain bounds. It can also compare this ratio to other known ratios (e.g., for previous sensors). It can also look to see if the ISIG after calibration is above/below a certain range. These and other techniques can be utilized for this feature.

At the outset, the process 500 assumes that the two sensors generate measurements that are within a practical working tolerance of each other, e.g., less than a 10% difference. Consequently, the new sensor device can be initially trusted for purposes of therapy decisions. Moreover, the existing sensor data generated by the old sensor device can be taken as an accurate measurement of the analyte level of interest, such that the new sensor device can be calibrated based on the existing sensor data (rather than based on a new sample from the user). Over time, the new sensor device can be calibrated on its own based on analyte samples taken from the user, but the initial calibration can be seamlessly performed with no delay and with little to no user involvement.

In certain embodiments, the new analyte sensor device updates its status to indicate completion of the configuration/calibration procedure. After completion of the configuration/calibration, the process 500 continues by transitioning operation of the new analyte sensor device from its initialization mode to its measurement mode (task 516), during which the new analyte sensor device generates sensor signals that are indicative of the measured analyte level (e.g., blood glucose) of the user. There can be various manual or automatic triggers to activate the switch from the old to the new sensor device. For example, the old sensor device expires, the user initiates a change in the sensors, or a time-based trigger can be implemented. Notably, the generated sensor signals will already be calibrated to some extent, and ongoing operation of the new analyte sensor device in its measurement mode can include further calibration based on analyte samples obtained from the user, such as fingerstick blood glucose measurements. After transitioning to the measurement mode of the new analyte sensor device, operation of the old analyte sensor device can be terminated (task 518). Task 518 may be automatically controlled by one or both of the sensor devices, by the linked medical device, and/or by the linked intermediary device. Alternatively, task 518 may be automatically performed when the old analyte sensor device is removed from the body of the user, when it becomes unpaired from the intermediary device, when it loses data connectivity with the new analyte sensor device, or the like. Thereafter, only the new analyte sensor device remains deployed, operating in its normal measurement mode. In the context of an insulin infusion system that includes a continuous glucose sensor, the process 500 allows a new sensor device to be quickly and conveniently initialized without requiring a blood sample, and in a way that does not result in suspension of the insulin infusion pump operation or suspension of certain operations, such as automatic closed loop control.

Although sensor calibration is described above, the system 100 and the process 500 can be utilized for other purposes with sensor devices that do not require user calibration, e.g., factory-calibrated sensor devices. In this regard, the transfer of sensor data between two sensor devices can be used to enhance sensing accuracy, reduce warm-up time, or otherwise improve sensor device performance even if the sensor device requires no calibration.

As explained above, the system 100 and the process 500 support different possible device topologies and arrangements. In accordance with the exemplary embodiment, an intermediary device with a display functions as the communication path for the two sensor devices, while also functioning as the primary display and user interface for the user. In an alternative implementation, an intermediary device merely serves as a display/interface device for the user, while the two sensor devices communicate directly with each other. In another embodiment, the system 100 need not include a display device or an intermediary device. In such an embodiment, the two sensor devices communicate directly with each other. It should be appreciated that other configurations and topologies can also be deployed with the system 100 if so desired.

Data Integrity

The configuration/calibration data may be transmitted in an unencrypted manner, e.g., as plaintext. Alternatively, the configuration/calibration data can be partially or fully encrypted to protect the data against interception from unauthorized parties. Some possible implementations include the following, without limitation:

The old sensor device provides a block of data to the display device that is encrypted using a first encryption key known to the old sensor device and the display device. The display device decrypts the data upon reception. The display device may re-encrypt the data with a second encryption key known to the display device and the new sensor device prior to transmission to the new sensor device. The new sensor device decrypts the data upon reception.

The old sensor device provides a block of data encrypted with a key not known to the display device, but known to the new sensor device. The display device transfers the encrypted data to the new sensor device. The new sensor device decrypts the data upon reception. This embodiment may prevent the display device from inspecting or altering the contents of the sensor-provided data.

The old sensor device directly transmits a block of data to the new sensor device. The data is encrypted with a key known to both of the sensor devices.

The configuration/calibration data may include checksums or hashes to protect the data against corruption. The configuration/calibration data may include cryptographic signatures to protect the data against tampering. Signatures may be computed using symmetric-key or public-key cryptosystems. The calibration data may include validity timestamps to allow the display device or the new sensor device to reject data that exceeds an age limit.

Automated Wireless Pairing

As explained above, a wireless transmitter may be required to send readings from a glucose sensor to an insulin pump or smartphone (e.g., using the BLUETOOTH wireless data communication standard). The transmitter is paired with the pump or smartphone via user input. In accordance with conventional designs, the RF transmitters mechanically attach to the glucose sensor. When the sensor expires (e.g., in one or two weeks), the RF transmitter is mechanically attached to the new sensor. According to modern sensor designs, RF transmitters are built inside the glucose sensor, yielding benefits associated with a smaller form factor. When the sensor expires, the user must unpair the RF transmitter from the pump (or smartphone) and pair the new RF transmitter before starting use of a new sensor.

In certain practical implementations, the user must first unpair the RF transmitter from the pump. Next, the user can pair a new transmitter. Once the RF pairing is complete, the user can initialize and calibrate the new sensor. This step can take up to two hours. This weekly (or biweekly) pairing process adds to the already burdensome process of maintaining glucose control while switching to a new sensor. These mandatory steps can yield hours without sensor protection from hypoglycemia (e.g., "Suspend on Low" technology) and the pump cannot provide closed loop therapy without a calibrated sensor. Thus, having an RF transmitter disposed with every glucose sensor may not be a benefit to the user under these circumstances.

Given that RF transmitters and glucose sensors can be implemented with the same disposable device, a secure and seamless sensor management scheme is proposed. This produces less user burden than current products, more protection from hypoglycemia, and data collection for sensor quality control. The proposed methodology employs device key management by software, and assumes that the insulin pump (or smartphone) has a linked user account (e.g., an account suitable for use with patient status monitoring or recordkeeping).

Figure 6:
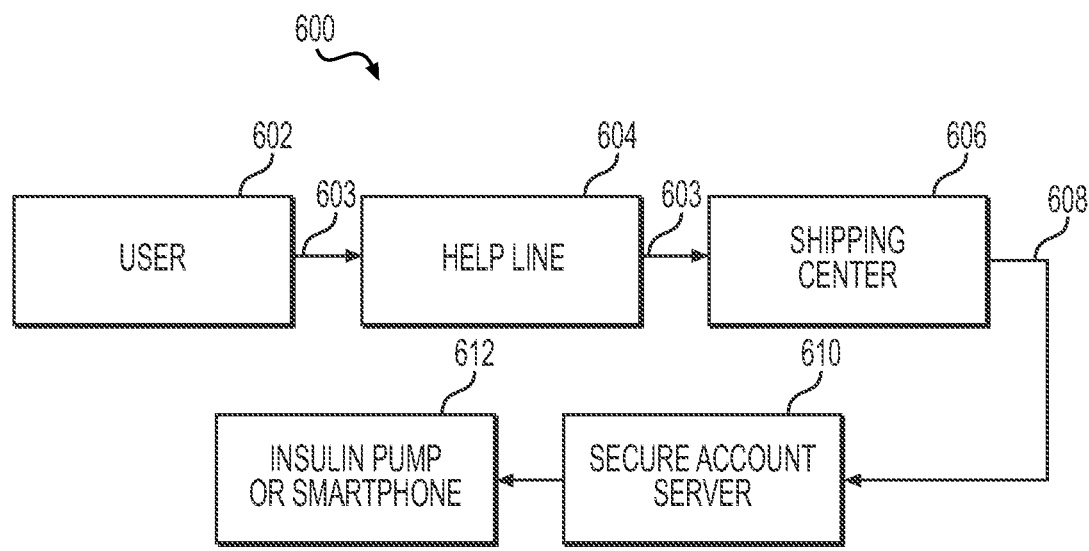
FIG. 6 is a block diagram that illustrates a device key management scheme.

Feature 1: When the user account orders new sensors, the factory provides the shipped sensors' serial numbers to a secure account server. This secure server generates encrypted keys for each serial number, and provides them to the linked insulin pump (or smartphone). In this regard, FIG. 6 is a block diagram that illustrates a device key management scheme 600. For this example, the user 602 or user account generates a request 603 or order for new sensors by contacting a help line 604. The request 603, which may include a user or account identifier, is forwarded to a shipping center 606. The shipping center 606 provides the serial numbers 608 of the shipped sensor devices (along with the user/account identifier) to a secure account server 610. The server 610 responds by sending encrypted authorization keys for each sensor device to the insulin pump or smartphone 612 that is linked to the user/account identifier.

Feature 2: When the new sensor device is attached to the user's body it enters a "search mode" by broadcasting its serial number in an encrypted format. Only the device with the preassigned matching keys can reply successfully, ending the search mode. This adds the security required for pairing the new sensor device with another device without user involvement.

Feature 3: The newly paired sensor silently begins warm-up and does not request calibration unless the previous sensor has expired. Thus, the new sensor is deployed while the old sensor remains active, and both sensors operate in an "overlapping" manner during a period of time. Should the user provide a blood glucose value, this calibrates the new sensor. Upon successful calibration of the new sensor, the user is informed that they can remove the old sensor. In practice, the user can be notified via a single displayed screen or message on the infusion pump or monitoring device. In contrast, the conventional routine for replacing an old glucose sensor device might require extensive patient involvement and interaction with many different display screens.

Figure 7:
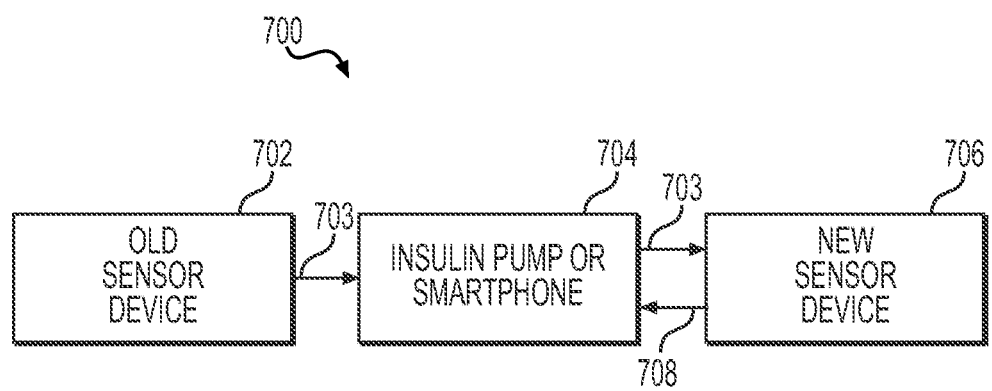
FIG. 7 is a block diagram that illustrates a sensor pre-calibration scheme.

Feature 4: Enhanced protection from low glucose state during sensor replacement. Given the new sensor is inserted before the previous sensor expires, the insulin pump (or smartphone) shares the old sensor's glucose values with the new sensor. These shared glucose values are used for pre-calibration, a sufficient state for providing low glucose detection from the new sensor (should the old sensor expire). Thus, if the user is sleeping, they can still be alerted in response to a detected low glucose condition, and the insulin pump can continue to provide automated suspend therapy. The sensor glucose values for the pre-calibrated sensor will not be shown to the user. If a fingerstick blood sugar value is provided to the pump (or smartphone), that value can be given to the new sensor for fast calibration. In this regard, FIG. 7 is a block diagram that illustrates a sensor pre-calibration scheme 700. The old sensor device 702 sends its glucose values 703 to the insulin pump or smartphone 704, which forwards the glucose values 703 to the new sensor device 706 for use as pre-calibration values. The new sensor device 706 calibrates itself using the glucose values 703 and generates its own glucose values 708 that are suitable for use by the insulin pump or smartphone 704 to provide low protection during a period of time following deployment of the new sensor device 706. Thus, even if the old sensor device 702 expires, the new sensor device 706 can provide sufficient low glucose protection using the pre-calibration scheme.

Feature 5: The keys provided to the insulin pump (or smartphone) for each sensor also include the sensor's manufacturing date and location. If the user inserts a sensor that is too old (shelf life expired), a warning is given to the user. When each sensor expires (or is otherwise ready for replacement) the reason "code" is saved to history (e.g., the user's account history). As a result, the parent company has the following quality control information: sensor serial number, manufacturing date, and manufacturing location; sensor start date; sensor performance data; and sensor decommission or replacement reason.

Benefits and Results

Continuous Glucose Monitoring (CGM) can be truly continuous: glucose alerts, and low glucose suspends remain active. There is no downtime for device removal, un-pairing, new device pairing, starting sensor, warmup (which usually might take up to 2 hours) and calibration (which usually might take up to 12 minutes). This also provides more time in automatic glucose control modes (with potentially improved outcomes).

The user can attach a new sensor at bedtime and trust that a "suspend before low" function can utilize both the expiring sensor and the new sensor.

Data collection is automated for end-to-end quality control of the sensor.

The automated sensor changeover eliminates a significant amount of user activity from occurring every 1-2 weeks. These changes significantly reduce time-on-task and burden.

Device Roles

In some embodiments, the display device acts as a data pass-through device. It does not include logic for determining the efficacy of the calibration data. The new sensor device determines whether the calibration data is satisfactory for use in calibrating the new sensor device. In other embodiments, the display device may check the validity of the calibration data payload or augment it with additional information, such as data generated or maintained by the medical device, status data, or the like. In other embodiments, no display device is present in the system 100.

Mechanisms of Data Transfer

The configuration/calibration data may be transferred via a wireless network, such as a BLUETOOTH network link, Wi-Fi, or another technology. The data may also be transferred through other means of wired or wireless communication. The data may be relayed through a display device or transferred directly between two sensors. It may also be relayed via two different display or intermediary devices (for example, when a patient is using one sensor device with an insulin infusion pump and wishes to change to a second sensor device monitored by a smartphone).

Other Applications

The data transfer mechanisms and workflows described herein may be employed in CGM systems not requiring the end user to provide calibration data ("factory calibrated"). For these systems, the data transferred may instead be used to improve the performance of the new sensor device. Possible applications include the following, without limitation: reducing the duration of the warmup period for the new sensor device; improving the accuracy of initial sensor measurements from the new sensor device; early detection of problems or performance issues with the old sensor device.

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A method of automatically initializing an analyte sensor for a user, the method comprising the steps of:
    operating a first analyte sensor in a first measurement mode to generate first sensor signals indicative of an analyte level of the user;
    deploying a second analyte sensor to measure the analyte level of the user;
    operating the second analyte sensor in an initialization mode, concurrently with operation of the first analyte sensor in the first measurement mode, to receive sensor configuration data generated by the first analyte sensor;
    determining, by the second analyte sensor, whether the received sensor configuration data is suitable for calibrating the second analyte sensor; and
    responsive to determining that the received sensor configuration data is unsuitable for calibrating the second analyte sensor, causing generation of a message prompting the user to obtain an analyte sample.

2. The method of claim 1, wherein the second analyte sensor receives the sensor configuration data directly from the first analyte sensor.

3. The method of claim 1, wherein the second analyte sensor receives the sensor configuration data from an intermediary device that communicates with the second analyte sensor.

4. The method of claim 3, wherein the intermediary device comprises a medication infusion device configured to regulate delivery of medication to the user based on sensor signals generated by the first analyte sensor or the second analyte sensor.

5. The method of claim 3, wherein the intermediary device comprises a mobile computing device.

6. The method of claim 3, further comprising the step of pairing the second analyte sensor with the intermediary device to facilitate transmission of the sensor configuration data from the intermediary device to the second analyte sensor.

7. The method of claim 1, further comprising:
    in response to determining that the received sensor configuration data can be used for calibrating the second analyte sensor, during operation of the second analyte sensor in the initialization mode, calibrating the second analyte sensor with at least some of the received sensor configuration data; and after the calibrating, transitioning operation of the second analyte sensor from the initialization mode to a second measurement mode during which the second analyte sensor generates second sensor signals indicative of the analyte level of the user.

8. An analyte sensor device comprising:

a housing;

an electronics assembly inside the housing; and a sensor element extending from the housing and electrically coupled to the electronics assembly, wherein the sensor element provides sensor signals indicative of an analyte level of a user when the analyte sensor device is deployed at the user;

the electronics assembly comprising at least one processor device and non-transitory processor-readable media operatively associated with the at least one processor device, the processor-readable media comprising executable instructions configurable to cause the at least one processor device to perform a method comprising the steps of:

activating an initialization mode of the analyte sensor device;

during operation of the analyte sensor device in the initialization mode, receiving sensor configuration data for processing by the electronics assembly, the sensor configuration data originating at a second analyte sensor device deployed at, or previously deployed at, the user;

determining whether the received sensor configuration data is suitable for calibrating the analyte sensor device; and responsive to determining that the received sensor configuration data is unsuitable for calibrating the analyte sensor device, causing generation of a message prompting the user to obtain an analyte sample.

9. The analyte sensor device of claim 8, wherein:

activating the initialization mode of the analyte sensor device is performed while the second analyte sensor device is deployed at the user, and while the second analyte sensor device is operating in a second measurement mode during which the second analyte sensor device generates second sensor signals indicative of the analyte level of the user; and operation of the analyte sensor device in the initialization mode is performed concurrently with operation of the second analyte sensor device in the second measurement mode.

10. The analyte sensor device of claim 8, wherein the analyte sensor device receives the sensor configuration data directly from the second analyte sensor device, or indirectly from an intermediary device that communicates with the analyte sensor device.

11. The analyte sensor device of claim 8, further comprising:

in response to determining that the received sensor configuration data can be used for calibrating the analyte sensor device, during operation of the analyte sensor device in the initialization mode, configuring at least one sensor parameter of the analyte sensor device, based on the received sensor configuration data; and after the configuring, transitioning operation of the analyte sensor device from the initialization mode to a measurement mode during which the analyte sensor device generates sensor signals indicative of the analyte level of the user.

12. The analyte sensor device of claim 11, wherein the configuring comprises calibrating the analyte sensor device using at least some of the received sensor configuration data.

13. A method of automatically initializing an analyte sensor for a user, the method comprising the steps of:

activating a new analyte sensor to measure an analyte level of the user;

during operation of the new analyte sensor in an initialization mode, receiving sensor configuration data at the new analyte sensor, the sensor configuration data originating at an old analyte sensor deployed at, or previously deployed at, the user;

determining whether the received sensor configuration data is suitable for calibrating the new analyte sensor; and responsive to determining that the received sensor configuration data is unsuitable for calibrating the new analyte sensor, causing generation of a message prompting the user to obtain an analyte sample.

14. The method of claim 13, wherein activating the new analyte sensor is performed while the old analyte sensor is deployed at the user and operating in a second measurement mode during which the old analyte sensor generates second sensor signals indicative of the analyte level of the user.

15. The method of claim 14, wherein operation of the new analyte sensor in the initialization mode is performed concurrently with operation of the old analyte sensor in the second measurement mode.

16. The method of claim 14, wherein the new analyte sensor receives the sensor configuration data directly from the old analyte sensor.

17. The method of claim 13, wherein the new analyte sensor receives the sensor configuration data from an intermediary device that communicates with the new analyte sensor.

18. The method of claim 17, wherein the intermediary device comprises a mobile computing device.

19. The method of claim 17, further comprising the step of pairing the new analyte sensor with the intermediary device to facilitate transmission of the sensor configuration data from the intermediary device to the new analyte sensor.

20. The method of claim 13, wherein:

determining, by the new analyte sensor, whether the received sensor configuration data can be used for calibrating the new analyte sensor is based on a sensor glucose value determined by the old analyte sensor and a sensor signal determined by the new analyte sensor;

in response to determining that the received sensor configuration data can be used for calibrating the new analyte sensor, during operation of the new analyte sensor in the initialization mode, configuring at least one sensor parameter of the new analyte sensor, based on the received sensor configuration data; and after the configuring, transitioning operation of the new analyte sensor from the initialization mode to a first measurement mode during which the new analyte sensor generates first sensor signals indicative of the analyte level of the user.

* * * * *